United States Patent [19]

Kludas

[11] Patent Number: 5,036,056
[45] Date of Patent: Jul. 30, 1991

[54] METHODS FOR TREATING DAMAGED CORNEAL, UTERINE, OR CARTILAGE TISSUE

[76] Inventor: Martin Kludas, Herthastrasse 22, D-1000 West Berlin-33, Fed. Rep. of Germany

[21] Appl. No.: 500,330

[22] Filed: Mar. 27, 1990

Related U.S. Application Data

[63] Continuation of Ser. No. 70,991, Jul. 8, 1987, abandoned.

[51] Int. Cl.$^5$ .................. A61K 31/715; C07H 5/04
[52] U.S. Cl. ................................. 514/54; 514/912; 514/935; 536/55.1; 536/55.2
[58] Field of Search ............... 536/55.1, 55.2; 514/54, 514/912, 935; 424/59

[56] References Cited

U.S. PATENT DOCUMENTS

| Re. 30,239 | 3/1980 | Kuettner et al. | 424/569 |
|---|---|---|---|
| 3,839,590 | 10/1974 | Battista | 514/773 |
| 3,887,703 | 6/1975 | Manoussos | 424/581 |
| 3,991,184 | 11/1976 | Kludas et al. | 514/21 |
| 4,042,457 | 8/1977 | Kuettner et al. | 424/548 |
| 4,108,849 | 8/1978 | Thomas | 530/395 |
| 4,228,153 | 10/1980 | Burov et al. | 514/774 |
| 4,296,099 | 10/1981 | Berrebi et al. | 424/582 |
| 4,327,078 | 4/1982 | Charlet et al. | 424/45 |
| 4,389,487 | 6/1983 | Ries | 435/273 |
| 4,420,339 | 12/1983 | Kato | 106/124 |
| 4,448,718 | 5/1984 | Yannas et al. | 530/356 |
| 4,451,397 | 5/1984 | Huc et al. | 530/356 |
| 4,464,362 | 8/1984 | Kludas et al. | 424/114 |
| 4,488,911 | 12/1984 | Luck et al. | 106/161 |
| 4,511,653 | 4/1985 | Play et al. | 435/68.1 |
| 4,642,292 | 2/1987 | Reid et al. | 435/240 |
| 4,664,110 | 5/1987 | Schanzlin | 606/20 |
| 4,696,813 | 9/1987 | Higa | 424/59 |

FOREIGN PATENT DOCUMENTS

| 128706A3 | 12/1984 | European Pat. Off. |
| 154447A2 | 9/1985 | European Pat. Off. |
| 1730 | 3/1963 | France |
| 6652 | 1/1969 | France |
| 2299019 | 8/1976 | France |
| 2487197 | 1/1982 | France |
| 2591107 | 6/1987 | France |
| 1386864 | 2/1972 | United Kingdom |

*Primary Examiner*—Catherine S. Kilby Scalzo
*Attorney, Agent, or Firm*—Pennie & Edmonds

[57] ABSTRACT

Methods for treating damaged corneal, uterine or cartilage tissue comprising applying a therapeutically effective amount of a composition comprising:

(a) a sterile extracellular connective tissue matrix composition comprising collagens, proteoglycans, glycosaminoglycans and glycoproteins wherein said collagens, said proteoglycans, said glycosamino glycans, and said glycoproteins have each been extracted from an extracellular connective tissue matrix and are in their native structural form and (b) a pharmaceutically acceptable carrier.

31 Claims, No Drawings

METHODS FOR TREATING DAMAGED CORNEAL, UTERINE, OR CARTILAGE TISSUE

This is a continuation of application Ser. No. 07/070,991 filed July 8, 1987, now abandoned.

TABLE OF CONTENTS

1. Introduction
2. Background of the Invention
   2.1—Eye Structure
   2.1.1—Cornea Structure
   2.1.2 Damage to Cornea
   2.2—Extracellular Matrix
   2.3—Extracellular Membrane Treatment
3. Summary of the Invention
4. Description of the Invention
   4.1—Source, Composition and Extract Preparation
   4.2—Treatment of Damaged Corneal and Other Tissue
   4.3—Ophthalmic Formulations
   4.4—Ointment
   4.5—Aqueous Solution

1. INTRODUCTION

This invention relates to ophthalmic agents and compositions for the repair and remodeling of damaged corneal tissue. This invention also relates to a method for treating damaged corneal tissue with these agents and compositions.

Damage to the cornea can be attributed to a variety of factors. Some of these factors are ultraviolet radiation, aging, thermal and chemical burns (acid or alkali) and physical trauma. It is important from a therapeutic point of view to conserve an intact epithelial-matrix junction membrane and to assist in the rapid repair of damaged corneal tissue. Since a damaged cornea results in limited visual functionality.

The underlying problem addressed by the present invention has been the inability, to date, to provide a composition or treatment which would enable the repair damaged corneal tissue. This invention, therefore, relates to ophthalmic agents, compositions and methods for their use which, utilizing appropriate therapy, are effective in repairing and remodeling damage corneal tissue. More specifically, the ophthalmic agents utilized in this invention provide essential components of the extracellular connective tissue matrix in their natural or native, unaltered structural form, which provide a physiological matrix required to repair damaged corneal tissue. The result of treatment with these ophthalmic agents is a cornea wherein the normal physiological visual functioning has been restored.

2. BACKGROUND OF THE INVENTION

2.1 Eye Structure

The eye, apart from its physical shape, has many of the structural features of the camera. The eyelids compromise the shutter. The iris is a diaphragm which contacts and dilates automatically in relation to the amount of light available. The eye has a lens composed of altered transparent epithelial cells but which is more elastic than the glass lens of a camera. The lens of the eye, as opposed to a camera, is suspended in such a way that muscle action can alter its shape and so change its focal length. As a consequence, the eye need not be shortened or elongated when objects at different distances are successively brought into focus as is necessary in a camera with a rigid lens. The a camera has its counterpart in the eye in strong connective tissue membrane, the sclera. The counterpart in the eye of the light-sensitive film used in a camera is a membrane of living cells of nervous origin, the retina, which lines not only the back but the sides of the eye as well. Then, finally, just as black is used to blacken all the interior surfaces of a camera that might leak or reflect light, black pigment is distributed generously between the retina and the sclera and in other sites where it would be useful.

However, unlike many modern cameras, the lens of the eye is not placed at its very front. The eye has its external aperture covered with a "glass window to keep out the dust", and its lens inside, a short distance behind the glass window. The transparent window in the central part of the front of the eye is of a curved form and is called the cornea. This is composed chiefly of a tough but transparent type of the dense connective tissue that is continuous with the opaque connective tissue of the sclera that surrounds and supports the remainder of the eye.

The cornea plays a larger role than the lens in focusing the image upon the retina because light retina because light rays are bent more in passing from air into and out of the lens.

The surface of the cornea is curved so that light rays coming from a single point source hit the cornea at different angles and are bent different amounts. But all in such a way that they are directed to a point after emerging from the lens.

The shape of the cornea and lens and the length of the eyeball determine the point where light rays reconverge. Although the cornea performs the greater part quantitatively of focusing the visual image on the retina, all adjustments of distance are made by changing the shape of the lens. Such changes are called accommodation. The shape of the lens is controlled by a muscle which flattens the lens when distant objects are to be focused upon the retina and allows it to assume a more spherical shape to provide additional bending of the light rays when rear objects are viewed.

2.1.1 Cornea Structure

The cornea is the anterior part of the supporting layer of the eye. It is a transparent, nonvascular membrane. It has a shorter radius of curvature than the remainder of the wall of the eye. Since it is exposed, it is subject to cuts, abrasions and other kinds of trauma. It is important in treating injuries of the cornea to know its thickness. It is about 0.5 mm. thick at its central part and somewhat thicker at its periphery.

The cornea consists chiefly of a special kind of dense connective tissue, containing both cells and intercellular substance, called the substantia propria. This bordered anteriorly and posteriorly by a membrane of homogeneous intercellular substance. Anteriorly, the cornea is covered with stratified squamous nonkeratinizing epithelium and posteriorly it is lined by a single layer of endothelial cells.

The epithelium covering the cornea is several layers in thickness and is replete with nerve endings that are chiefly of the pain type. Their stimulation results reflexly in the blinking of the eyelids and in the flow of tears (mucus from the conjunctival glands also helps keep the corneal surface wet); if the nerve pathways concerned in the reflexes described above are destroyed, the corneal surface, on not being frequently wiped by the wet lids, becomes dry and then ulcerated. There are no papillae projecting into the epithelium of the cornea. Furthermore, since the connective tissue beneath it has no capillaries, the epithelium of the cornea is a comparatively long way from source of nutrition. The diffusion phenomenon on which its cells depend must be very efficient, for corneal epithelium, on being injured, regenerates rapidly. Carbon dioxide is eliminated through the corneal epithelium.

The membrane of intercelluar substance on which the basal cells of the corneal epithelium rests is called Bowman's membrane. This consists of a transparent homogeneous material. It is generally regarded as a condensation of the intercellular substance of the substantia propria. It contains some collagen and is regarded as an important protective layer, being resistant to trauma and bacterial invasion. Once destroyed, it does not regenerate. Bowman's membrane does not extend from the cornea into the sclera. The site at which cornea undergoes a transition into sclera and consequently, where Bowman's membrane ends is called the limbus.

The substantia propria comprises about 90 percent of the thickness of the cornea. It contains flattened connective tissue cells that are disposed between parallel bundles of collagenic fibers called lamellae. While most of the fibers in the lamella are disposed parallel with surface, those of one lamella run at an angle to those of the next. The fibers of some lamellae join with those of adjacent lamellae to bind the substantia propria together.

In the substantia propria the collagen fibrils and fibers are embedded in sulfated mucopolysaccharide containing proteoglycans and glycoproteins. It is assumed that the binding together of collagen fibrils in the substantia propria by the substance as well as their regular arrangement is responsible for the unique transparency of this membrane.

Deep to the substantia propria is Descement's membrane. This is composed of a special kind of material that appears to be homogeneous and seem to be chiefly an special form of collagen. Applied to the inner side of Descement's membrane is a single layer of endothelial cells; this layer is called Descement's endothelium.

2.1.2 Damage to Cornea

Trauma to the eye or adjacent structures requires meticulous examination to determine the extent of injury. The patient's vision, the range of extraocular motion, the location of lid and conjunctival lacerations and of foreign bodies, and the clarity of the ocular media should be carefully determined.

Conjunctival and corneal injuries by foreign bodies are the most frequent eye injuries. Seemingly minor trauma can be serious if ocular penetration is unrecognized or if secondary infection follows a corneal abrasion.

The treatment typically is adequate light, good anesthesia, and proper instruments are essential to ensure minimal trauma when removing embedded foreign bodies. Fluorescein staining renders foreign bodies and abrasions more apparent. An anesthetic is instilled onto the conjunctive. Both lids are everted and the entire conjunctiva and cornea inspected with a binocular lens (loupe). Conjunctival foreign bodies are lifted out with a moist sterile cotton applicator. A corneal foreign body that cannot be dislodged by irrigation may be lifted out carefully on the point of a sterile spud or hypodermic needle, under loupe magnification.

If the foreign body was tiny, only an antibiotic ointment (e.g., erythromycin 0.5% or bacitracin 500 u./gm) is typically instilled. If larger, however, treatment is that for any corneal abrasion is usually dilating the pupil with a short-acting cycloplegic, instilling an antibiotic, usually erythromycin or bacitracin; and applying a patch firmly enough to keep the eye closed overnight. The corneal epithelium regenerates rapidly; under a patch, large areas will heal within 1 to 3 days. Follow-up examination by an ophthalmologist 1 or 2 days after injury is wise, especially if the foreign body was removed with a needle or spud.

Chemical burns of the cornea and conjunctiva can be serious and are usually treated immediately by copious irrigation with water or other bland fluids. The eye may be anesthetized, if it is available, but irrigation should never be delayed and should be carried out for 5 to 30 min. depending on the estimate of chemical contact. Irrigation until the pH is neutral (as measured with paper indicators) is a reasonable end-point. Pain results from loss of corneal epithelium and chemical iritis, which is usually treated by instilling a long-acting cycloplegic, applying an antibiotic ointment, and patching. Initially, pain may require codeine 30 to 60 mg orally or meperidine 50 mg IM q 4 h. Severe burns require specialized treatment by an ophthalmologist to save vision and prevent major complications such as iridocyclitis, perforation of the globe, and lid deformities.

Various other forms of damage to the cornea may also occur in other fashions.

In superficial punctuate keratitis scattered, fine, punctuate loss of epithelium from the corneal surface may occur in one or both eyes. It is often associated with trachoma, staphylococcal blepharitis, conjunctivitis, or a respiratory tract infection. It may be due to a viral infection or may be a reaction to local medication and is commonly the cause of intense pain after exposure to ultraviolet rays (e.g., from welding arcs, sun lamps). Symptoms include photophobia, pain, lacrimation, conjuctival injection, and diminution of vision. An enlarged preauricular node may be present in viral cases. Lesions due to ultraviolet ray exposure do not appear until several hours after the exposure; they last 24 to 48 h. while those secondary to viral or bacterial agents may last for months. Healing is spontaneous and residual vision impairment is rare, regardless of etiology. Typically topical antimicrobial therapy is given promptly, particularly if a causative organism can be cultured and identified. A systemic analgesic may be needed for control of pain.

In corneal ulcers a local necrosis of corneal tissue is due to invasion by microorganisms. A pneumococcal, streptococcal, or staphylococcal infection following trauma or complicating a corneal foreign body is the usual primary cause. Corneal ulcers also occur as complications of herpes simplex keratitis, chronic blepharitis, conjunctivitis (especially bacterial), trachoma, dacryocystitis, gonorrhea, and acute infectious diseases. Pain, photophobia, blepharospasm, and lacrimation are usually present, but may be minimal.

Ulceration without extensive infiltration may occur in herpes simplex. Fungal ulcerations are densely infiltrated and show occasions discrete islands of infiltrate (satellite lesions) at the periphery. The deeper the ulcer, the more severe the symptoms and complications. Ulcers deep enough to involve Bowman's membrane and the substance of the cornea heal with fibrous tissue replacement, causing opaque scarring of the cornea and decreased vision. Phlyctenular Keratoconjunctivitis is a form of conjunctivitis, usually occurring in children, characterized by discrete nodular areas of inflammation (phlyctenules) and resulting from the atopic reaction of hypersensitive conjunctiva or cornea to an unknown allergen. Proteins of staphylococcal, tuberculous, or other bacteria origin have been implicated. The disease is rare in the U.S.A.

Interstitial keratitis is a form of a chronic nonulcerative infiltration of the deep layers of the cornea, with uveal inflammation. It is rare in the U.S.A. Most cases occur in children as late complication of congenital syphilis. Ultimately, both eyes may be involved. Rarely, acquired syphilis or tuberculosis may cause a unilateral form in adults. Photophobia, pain, lacrimation, and gradual loss of vision are common. The lesion begins in the deep corneal layers; soon the entire cornea develops a ground-glass appearance, obscuring the iris. New blood vessels grow in from the limbus and produce orange-red areas ("salmon patches"). Iritis, iridocyclitis, and choroiditis are common.

Keratomalacia is a condition associated with vitamin A deficiency and protein-calorie malnutrition, characterized by a hazy, dry cornea that becomes denuded. Corneal ulceration with secondary infection is common. The lacrimal glands and conjunctiva are also affected. Lack of tears cause extreme dryness of the eyes, and foamy Bitot's spots appear on the bulbar conjunctiva. Night blindness may be associated. Antibiotic ointments or sulfonamides (e.g., sulfacetamide ophthalmic solution 30% or ointment 10%) are required if secondary infection exists.

Keratoconus is a slowly progressive ectasia of the cornea, usually bilateral, beginning between ages 10 and 20. The cone shape that the cornea assumes causes major changes in the refractive power of the eye, necessitating frequent change of spectacles. Contact lenses provide better visual correction, and should always be tried when eyeglasses are not satisfactory. Surgery may be necessary if the cornea becomes thin or if scarring follows rents in the posterior corneal surface.

Bullous keratopathy is a condition caused by excessive fluid accumulation in the cornea, most frequently the result of aging and failure of the posterior corneal endothelium. It is seen occasionally after intraocular operations (e.g., for cataract), where the mechanical stresses further interfere with the process of corneal detumescence.

2.2 Extracellular Matrix

Most cells in multicellular organisms are in contact with an intricate meshwork of interacting, extracellular macromolecules that constitute the extracellular matrix. These versatile protein and polysaccharide molecules are secreted locally and assemble into an organized meshwork in the extracellular space of most tissues. In addition to serving as a type of universal biological glue, they also form highly specialized structures such as cartilage, tendons, basal laminae, and (with the secondary deposition of a form of calcium phosphate crystals) bone and teeth.

Until recently, the vertebrate extracellular matrix was thought to serve mainly as a relatively inert scaffolding that stabilized the physical structure of tissues. But now it is clear that the matrix plays a far more active and complex role in regulating the behavior of the cells that contact it—influencing their development, migration, proliferation, shape, and metabolic functions.

The macromolecules that constitute the extracellular matrix are secreted by local cells, especially fibroblasts, which are widely distributed in the matrix. Two of the main classes of extracellular macromolecules that make up the matrix are (1) the collagens and (2) the polysaccharide glycosaminoglycans, which are usually covalently linked to protein to form proteoglycans. The glycosaminoglycan and proteoglycan molecules form a highly hydrated, gel-like "ground substance" in which collagen fibers are embedded. While the long collagen fibers strengthen and help to organize the matrix, the aqueous phase of the polysaccharide gel permits the diffusion of nutrients, metabolites, and hormones between the blood and the tissue cells. In many cases, fibers of the rubberlike protein elastin are also present and impart resilience to the matrix. In addition, two high molecular weight glycoproteins are among the major components of extracellular matrices: fibronectin, which is widely distributed in connective tissues, and laminin, which has so far been found only in basal laminae.

The term connective tissue is often used to describe the extracellular matrix plus the cells found in it, such as fibroblasts, macrophages, and mast cells. The amount of connective tissue in organs varies greatly: the cornea, skin and bone are composed mainly of connective tissue, whereas the brain and spinal cord contain very little. Moreover, the relative amounts of the different types of matrix macromolecules and the way that they are organized within the extracellular matrix vary enormously, giving rise to a diversity of forms, each highly adapted to the functional requirements of the particular tissue. Thus, the matrix can become calcified to form the rock-hard structures of bone or teeth, it may take on the ropelike organization of the collagen fibers in tendons, which gives them their enormous tensile strength, or it can form a clear window-like structure in the cornea.

The collagens are a family of highly characteristic fibrous proteins found in all multicellular animals. They are the most abundant proteins in mammals, constituting 25% of their total protein. The central feature of all collagen molecules is their stiff, triple-stranded helical structure. Three collagen polypeptide chains, called alpha-chains, are wound around each other in a regular helix to generate a ropelike collagen molecule about 300 nm long and 1.5 nm in diameter. At most, eleven genetically distinct collagen types have been well defined.

The major types are referred to as types I, II, III, IV and V. Types I, II and III are the main types of collagen found in connective tissues, and of these, type I is much the most common, constituting about 75% of the collagen in the body. After being secreted into the extracellular space, types I, II and III collagen molecules assemble into ordered polymers called collagen fibrils, which are long (up to many microns), thin (10 to 300 nm in diameter), cablelike structures clearly visible in electron micrographs. Such fibrils are often grouped into larger bundles, which can be seen in the light microscope as collagen fibers several microns in diameter. Type IV molecules (the main collagen in basal laminae) and type V and VI (found in small amounts near basal laminae and interstitially) do not form cross-banded fibrils.

Tissue such as skin requires elasticity in addition to tensile strength in order to function. An extensive network of elastic fibers in the extracellular matrix of these tissues gives them the required ability to recoil after transient stretch. The main component of elastic fibers is elastin, a 70,000-dalton glycoprotein, which, like collagen, is unusually rich in proline and glycine but, unlike collagen, contains little hydroxyproline and no hydroxylysine.

Glycosaminoglycans, formerly known as mucopolysaccharides, are long, unbranched polysaccharide chains composed of repeating disaccharide units. They are now called glycosaminoglycans because one of the two sugar residues in the repeating disaccharide is always an amino sugar (N-acetylglucosamine or N-acetylgalactosamine). Glycosaminoglycans are highly negatively charged due to the presence of sulfate or carboxyl groups or both on many of the sugar residues. Seven groups of glycosaminoglycans have been distinguished by their sugar residues, the type of linkage between these residues, and the number and location of sulfate groups. They are hyaluronic acid (the only group in which none of the sugars is sulfated), chondroitin 4-sulfate, chondroitin 6-sulfate, dermatan sulfate, heparan sulfate, heparin, and keratan sulfate.

Hyaluronic acid (also called hyaluronate or hyalurouan) exists as a single, very long carbohydrate chain of several thousand sugar residues in a regular, repeating sequence of disaccharide units. Hyaluronic acid, however, is not typical of the glycosaminoglycans. First, the others tend to contain a number of different disaccharide units arranged in more complex sequences. Second, the others have very much shorter chains, consisting of fewer than 300 sugar residues. Third, all of the other glycosaminoglycans are covalently linked to protein to form proteoglycan molecules.

Proteoglycans are different from typical glycoproteins. Glycoproteins usually contain from 1% to 60% carbohydrate by weight in the form of numerous, relatively short (generally less than 15 sugar residues), branched oligosaccharide chains of variable composition, which often terminate with sialic acid. In contrast, proteoglycans are much larger (up to millions of daltons), and they usually contain 90% to 95% carbohydrate by weight in the form of many long, unbranched glycosaminoglycan chains, usually without sialic acid.

Non-collagen glycoproteins that are present in the extracellular matrix include fibronectin, a fiber-forming glycoprotein (about 5% carbohydrate by weight) composed of two disulfide-bonded subunits of 220,000 daltons each. Fibronectin exists as large aggregates in the extracellular space. While most of the protein is not directly bound to cells, some of it is bound to the surfaces of fibroblasts and other cells when they are grown in culture. Purified fibronectin has been shown to promote the adhesion of a variety of cell types to other cells, as well as to collagen and other substrates.

In sum, all cells in tissues are in contact with an intricate extracellular matrix. This matrix not only holds the cells together in tissues, and tissues together in organs, but it also influences the development, polarity, and behavior of the cells it contacts. The matrix contains three major fiber-forming proteins—collagen, elastin, and fibronectin—which are interwoven in a hydrated gel formed by a network of glycosaminoglycan chains. All of the macromolecules are secreted locally by cells in contact with the matrix.

The collagens are ropelike, triple-stranded, helical molecules that aggregate in long cablelike fibrils or sheets in the extracellular space. These fibrils in turn can assemble in a variety of highly ordered arrays. Elastin molecules form an extensive cross-linked network of fibers and sheets that can stretch and recoil, imparting elasticity to the matrix. Fibronectin molecules form fibers that promote cell adhesion. The glycosaminoglycans are a heterogeneous group of long, negatively charged polysaccharide chains that (except for hyaluronic acid) are covalently linked to protein to form giant proteoglycan molecules. All of these matrix proteins and polysaccharides are thought to interact and to assemble in a large variety of different three-dimensional structures, ordered in part by the cells secreting the matrix. Since the orientation of the matrix will in turn influence the orientation of the cells it contains, order is likely to be propagated from cell to cell through the matrix.

Research in the fields of cell biology and embryology has also shown that an extracellular connective tissue matrix consisting of genetically distinct collagen types, proteoglycans and structural glycoproteins has a significant influence on cell proliferation, mitogenesis and morphogenesis (Hay, *Mod. Cell. Biol.*, 2: 509, 1983; Bernfield et al. in: The Role of Extracellular Matrix in Development, A.R. Liss, New York, 1984). It has been postulated that there exists a "dynamic reciprocity" between the extracellular matrix on the one hand, and the cytoskeleton and the nuclear matrix on the other hand. The extracellular matrix is thought to exert physical and chemical influences on the geometry and the biochemistry of the cell via transmembrane receptors so as to alter the pattern of gene expression by changing the association of the cytoskeleton with the mRNA, and the interaction of the chromatin with the nuclear matrix. Bissel, et al., *J. Theor. Biol.*, 99: 31–68 (1982).

The following references provide additional information concerning the extracellular matrix and its interactions with other tissue or cellular components. See, Hay, Cell and Extracellular Matrix, *Modern Cell Biology*, 2: 509–548 (1983) and Kleinman, et al., Role of Collagenous Matrices in the Adhesion and Growth of Cells, *Cell Biol.*, 88 (3): 473–486 (1981).

These factors, when combined with the knowledge that these matrix macromolecules are further known to individually to affect the behavior of cells in culture, has lead the art to attempt to explore the contribution of the extracellular matrix in the development of eye (E. D. Hay, J. of Cellular Biochemistry, 27:143–156 (1985); the maintenance of its active structure (K. K. Svboda et al., J. Cell. Biol. 103:250(a) 1986) K. Nakayasu, Opthalmic Res., 18:1–10 (1986); and in wound repair (S. R. Gordon, J. Cell. Bio., 103:250(a) 1986; Zieske, J. of Cell. Bio., 103:251(a) (1986)) A. H. Simonsen et al., Exp. Eye Res., 35:287–292 (1982)).

2.3 Extracellular Membrane Treatment

To date the only application of components of the extracellular matrix has been in cosmetic skin preparations wherein individual active substances or combinations of isolated individual components of the extracellular matrix are often used in the hope of preventing skin aging by substitution of deficient or damaged skin components.

For instance, skin preparations are disclosed in the German Patent No. DE-PS 20 64 604. This reference speaks of increasing the soluble, i.e. not cross-linked portion of the collagen in the skin, by using native soluble collagen (tropocollagen) to improve the age-dependent ratio of soluble to insoluble collagen in favor of the soluble fraction, and to slow down the loss of elasticity of the skin.

A cosmetic preparation containing collagen of the basement membrane is also disclosed in German Patent No. DE-PS 30 46 133. In contrast to the use of the interstitial collagen types I, II and III which are structurally similar to each other, the use of the basement membrane collagen (collagen type IV) is therein claimed to have a higher effectiveness, since said basement membrane collagen is adopted better by the cells. The stated object of using basement membrane collagen was to promote regeneration and faster growth of new skin cells. Thus the cosmetic preparation tries to counteract a feature of skin aging by supplying an individual substance.

U.S. Pat. No. 4,451,397 discloses the use of collagen in connection with mucopolysaccharides for cosmetic purposes. The main subject matter of the invention disclosed in this patent is a method for producing a solution or a homogeneous gel composition consisting of the aforementioned substances, and the use of these substances in a cosmetic preparation to improve skin tone. Chemical Abstracts, Vol. 101, 1984, No. 78679 b discloses a cosmetic preparation containing fibronectin, which serves as a nutrient for the skin.

Other references additionally disclose the use of connective tissue components for skin treatment. U.S. Pat. No. 3,991,184 to Kludas discloses the use of untreated, soluble collagen having an unchanged substantially non-cross-linked structure for use in treating the skin. U.S. Pat. No. 4,327,078 to Charlet et al. discloses cosmetic agents containing, as an active ingredient, soluble elastin for treatment of aging skin. In addition, U.S. Pat. No. 4,464,362 discloses cosmetic compositions containing inactive cultures of bacteria of the genus Bifidobacterium or bacteria related to this genus for promoting DNA repair in skin cells.

The hitherto known cosmetic agents and the active substances and combinations of different individual substances which have been used, however, have so far not considered the latest findings of research in connective tissue and cell biology in application to corneal injury.

Therefore, it is an object of the present invention to assist in the repair of corneal tissue visual functioning via a reconstituted, repaired, and remodeled corneal tissue.

3. SUMMARY OF THE INVENTION

The present invention provides a novel ophthalmic agent comprised of a sterilized extracellular connective tissue matrix wherein all of the extracted components are in the same structural form in which they existed in vivo and are in the same physiological proportions to each other in which they existed in vivo. It is also an aspect of this invention that this ophthalmic agent be combined with a pharmaceutically acceptable carrier to form an ophthalmic composition. This invention also provides for the utilization of the ophthalmic agent or composition in a method for treatment of aged or damaged corneal tissue, so as to result in a repair of the cornea. It is a goal of this treatment that the cornea will improve in healing rate as a result of application of the ophthalmic agent or composition. The precise details of the invention will be further described below.

4. DESCRIPTION OF THE INVENTION

4.1 Source, Composition and Extract Preparation

According to the present invention, damaged corneal tissue is provided with the essential components as extracts of the extracellular connective tissue matrix in their native in vivo structural form as a novel ophthalmic agent. These components are provided in their naturally occurring physiological proportions as represented in their particular extracellular connective tissue matrix source.

Surprisingly, it has been discovered that topical application of the essential components of an extract of the extracellular connective tissue matrix in physiological proportions leads to a repair of the corneal tissue damaged by aging or environmental factors such as ultraviolet light, heat or chemical (acid or alkali burns or physical trauma. Normal corneal structure is restored with the application of the opthalmic agent.

The structure and composition of the essential components of the extracellular connective tissue matrix in physiological proportions and in their native structural form in vivo according to the present invention can be illustrated by one process set forth below for their preparation. This procedure is merely an exemplary way to extract the essential components of the extracellular connective tissue matrix in their native structural forms and in the same proportion as their proportions in vivo. The reference, Miller, E. J. et al., preparation and characterization of the different types of collagen, *Methods in Enzymology*, 82 Part A: 33–64 (1982) also discloses extraction methods useful in preparation of the extract of this invention.

Fetal or fetal associated membranes of mammals which are preferably used as starting material can be, for example, placenta, blood vessels and umbilical cords as a sole source or in admixture with each other. The mammalian membrane source may be mammals such as cows (bovine), sheep (ovine), or pigs (porcine).

First, the tissue is rinsed with water to remove the blood. The tissue is then defatted, preferably with acetone, frozen preferably in liquid nitrogen and minced in a mill, e.g. in a blender. The disintegrated tissue obtained in this way is pre-treated with known protease inhibitors (as cited in Miller, supra) in appropriate buffer solutions of relatively high ionic strength. The purpose of said treatment is to minimize proteolysis by endogenous proteases, by inactivating the proteases. After an incubation, preferably for about one hour, the disintegrated tissue is separated, preferably centrifuged, and the sediment is thoroughly washed with water, preferably at ambient temperature.

The tissue mass treated in this way is solubilized by adjusted and graduated steps of extraction to obtain native components in the same physiological proportions as in the original membrane source.

In the first extraction step, the native, acid-soluble collagen molecules of types I and III are extracted preferably at about 4° C. under acidic condition (preferably of less than pH5) and low ionic strength according to methods known in the art. (Piez et al., Biochemistry 2, 58 (1963); Orekhovitch et al., Biockhimya 13, 55 (1948); Kulonen et al., Proc. Soc. Exp. Biol. Med. 84, 424 (1954); Gallop, Arch. Bioch. Bioph. 54, 486 (1966)). Acetic acid, preferably of a concentration of about 0.1 to 0.5M, is preferably used as extracting agent. However, formic acid of the same concentration, or acidic phosphate or citrate buffer, preferably at a concentration of 0.15 to 1.0M, may also be used.

The suspension containing the collagen is separated preferably by centrifugation and the sediment is washed in de-ionized water preferably about five times.

The washed sediment is then subsequently extracted to obtain proteoglycans and glycoproteins, such as fibronectin and laminin, and other known extracellular matrix components according to methods known in the art (cf. Sajedera et al., J. Biol. Chem. 244, 77 (1969)) preferably using salt solutions of high ionic strength, such as 1M NaCl. However, other salt solutions, such as 2M $MgCl_2$, 2M to 4M guanidine hydrochloride or 5M urea, may also be used.

The suspension obtained in this step is separated preferably by centrifugation. The supernatant, which is retained, contains the desired solubilized components in their native form. The sediment is again thoroughly washed in de-ionized water preferably about five times.

In a third extraction step, collagen of types IV, V, VI and VII, and collagens of types I and III which are more cross-linked and which could not be extracted in the first extraction step by the method described herein, are solubilized by a limited proteolysis, preferably using pepsin, preferably at temperatures from about 4 to about 18° C. (Miller et al., Biochemistry 11, 4903, 1972). The extract is separated preferably by centrifugation.

Preferably the proteolytic extraction step is repeated in order to obtain an extraction which results in a complete solubilization of the starting material.

Each individual extract obtained by the three extraction steps described above is adjusted to a pH-value of preferably 4.5 to 5.0. The extracts are then mixed by constant stirring at a low temperature, preferably about 4° C., until a homogeneous phase is obtained.

The mixture obtained in this way is the inventive ophthalmic agent of the extracellular connective tissue matrix extract in physiological proportions and in their native form. These solubilized components are present in macromolecular aggregates. Since this composition is for use in the eye, it is preferable that prior to application, it be sterilized by any number of methods known to those of skill in the art.

4.2 Treatment of Damaged Corneal and Other Tissue

The ophthalmic agent, as disclosed below, may be mixed with a pharmaceutically acceptable ophthalmic carrier to form a ophthalmic composition which may be directly or topically applied to the cornea. This ophthalmic composition or ophthalmic agent may be applied to the cornea in biologically or therapeutically effective amounts over a period of time which is sufficient to result in repair or remodeling of the cornea tissue. This repair or remodeling will typically be apparent from a decrease in the time needed for the healing process to repair the cornea tissue.

The particular amount of ophthalmic agent or composition to be applied to the cornea and the duration or number of applications can be determined by an ophthalmologist on an individual basis by utilizing the agent or composition until a visible improvement of the corneal tissue results. One skilled in the art of ophthalmology and who is familiar with standard treatment of corneal injures means would also be in a position to easily evaluate a beneficial course of treatment. Examples of typical and preferable treatments would be application two or three times a day with a ophthalmic composition containing about 10% of the ophthalmic agent.

The percentage of ophthalmic agent present in the composition would vary, of course, depending upon the carrier and the severity of the corneal damage to be treated by the agent.

It is also within the scope of this invention that the sterile opthalmic agent or composition may be utilized in methods of treating damage to other tissues of the human body. For instance, it is within the scope of this invention that the Application of the above agent or composition to a torn or otherwise damaged cartilage (i.e. cartilage leisions or erosion of the articular cartilage) or joint via intra-articular injection would be helpful in the repair and healing process of the damage. For instance, an injection of this agent or composition may be useful in the treatment of arthritis. It is also foreseeable that this agent or composition would be useful in treatment of other disease states, such as those involving the treatment of uterine conditions. Specifically, one possible application of this agent or composition would involve treating conditions of the endometrium or portio of the uterus. For instance, a application of this agent or composition may be useful in the re-epithielization of the portio of the uterus. The method of application or delivery of this agent or composition to the uterus would be in a standard manner known to those of ordinary skill in the medical arts.

4.3 Ophthalmic Formulations

The term "ophthalmic" or "ophthalmic composition" as used herein is intended to include all types of products which are applied in any manner directly to the person and is intended to include, in addition to the ophthalmic agent invention disclosed herein, conventional pharamceutically acceptable carriers such as water, saline and polyethelene glycol.

Said compositions may take the form of fatty or emulsions of the water-in-oil or oil-in-water types, gels or jellies, colloidal or non colloidal aqueous or oily solutions.

The amount of active ingredient contained in ophthalmic compositions according to the invention applied to the cornea may vary between wide limits, depending from the formulation and the frequency of use of said compositions. Generally, said compositions contain from 0.1%–99% by weight of the extracellular connective tissue matrix extract. Preferably the extracellular connective tissue matrix extract is in a sterile form.

The ophthalmic compositions used in the method according to the invention may also contain conventional antibiotic, anti-inflammatories, ophthalmic lubricants such as carboxymethyl cellulase, or anesthetics. More specifically, it is foreseeable in the practice of this invention that the sterile extracellular matrix may be combined with the following antibiotics or antiviral compounds (typically in drop or ointment form with the preferred indicated typical dosages):

| | |
|---|---|
| Ampicillin | — |
| Bacitracin | 20,000 units/ml |
| Carbenicillin | 4.0 mg/ml |
| Cefazolin | 50 mg/ml |
| Cephalothin | 50 mg/ml |
| Chloramphenicol | 5 mg/ml |
| Clindamycin | — |
| Colistin | 5–10 mg/ml |
| Erythromycin | 50 mg/ml |
| Gentamicin | 8–15 mg/ml |
| Lincomycin | — |

-continued

| | |
|---|---|
| Methicillin | — |
| Neomycin | 5–8 mg/ml |
| Penicillin G | 100,000 units/ml |
| Polymyxin B | 16,250 units/ml |
| Streptomycin | — |
| Sulfacetamide | 100–300 mg/ml |
| Tobramycin | 3 mg/ml |
| Vancomycin | 50 mg/ml |
| Idoxuridine (IDU) | — |
| Trifluridine | — |
| Vidarabine (Adenine Arabinoside, ARA-A) | — |
| Acyclovir (Acycloguanosine) | — |
| Pyrimethamine | — |
| Sulfadiazine | — |
| Corticosteroid preparation | — |
| Clindamycin | — |
| Amphotericin B | 2.5–10 mg/ml of diluent (distilled water of 5% dextrose solution) |
| Nystatin | Ointment 100,000 units/GM |
| Natamycin | 5% Suspension |
| Miconazole | — |

The following anti-inflammatories may also be utilized with the sterile extracellular matrix composition of this invention in solution or ointment form:
Hydrocortisone
Rednisolone
Dexamethasone The following topical anesthetics may also be used in combination with the extracellular matrix composition:
Cocaine Hydrochloride
Proparacaine Hydrochloride
Tetracaine Hydrochloride The following major component of demulcent (artificial tear) compositions may also be utilized in combination with the extracellular matrix composition:
Hydroxethylcellulose
Hydroxproplycellulose
Hydroxypropyl methylcellulose
Methylcellulose
Polyvinyl alcohol
Polyvinyl alcohol and cellulose ester
Polyvinyl alcohol and povidone
Other Polymeric Systems A few examples of ophthalmic compositions used in methods according to this invention are given hereafter. These examples are only illustrative and must not be considered as limiting the scope of the invention. In said examples, the percentages are by weight.

The following formulations are exemplary embodiments of the invention, but are not intended to limit the scope of this invention or restrict it to these particular formulations:

4.4 Ointment

An ointment and related compositions containing the active composition (extracellular connective tissue matrix extract prepared according to the present invention) may be formulated as follows:

| | | |
|---|---|---|
| (a) | Petrolatum, Liquid Lanolin, Mineral Oil | 90% |
| | or | |
| | Sterile ointment containing white petrolatum and mineral oil | 90% |
| | or | |
| | Sterile ointment with white petrolatum, liquid lanolin, mineral oil, methylparaben and polyparaben | 90% |
| | or | |
| | Sterile ointment containing white petrolatum and light mineral oil | 90% |
| | Sterile ointment with 42.5% mineral oil, 55% white petrolatum, and lanolin | (Total) 97.5% |
| | and | |
| (c) | active composition according to the present invention (prepared as explained above) | 10.0% |

4.5 Aqueous Solution

An aqueous solution containing the active composition (the extracellular connective tissue matrix extract prepared according to the present invention) may be formulated as follows:

| | | |
|---|---|---|
| (a) | active composition according to the present invention (as in example 1) and | 10.0% |
| (b) | Saline (NaCl) or a combination of an aqueous solution of salts such as Benzalkonium Chloride, Potassium Chloride, Disodium Edetate, Boric and Acid, Sodium Carbonate | 90% |

I claim:
1. A method of treating a damaged cornea comprising applying to said cornea a therapeutically effective amount of a composition comprising:
   (a) a sterile extracellular connective tissue matrix composition comprising collagens, proteoglycans, glycosaminoglycans and glycoproteins, wherein said collagens, said proteoglycans, said glycosaminoglycans, and said glycoproteins have each been extracted from an extracellular connective tissue matrix and are in their native structural form, and
   (b) a pharmaceutically acceptable carrier.
2. The method of claim 1 wherein the sterile extracellular connective tissue matrix composition and pharmaceutically acceptable carrier is applied topically.
3. The method of claim 1 wherein the sterile extracellular connective tissue matrix composition is derived from a mammal.
4. The method of claim 1 wherein the sterile extracellular connective tissue matrix composition is derived from an animal selected from the group consisting of bovine, ovine and porcine.
5. The method of claim 3 wherein the sterile extracellular connective tissue matrix composition is derived from the tissue selected from the group consisting of placenta tissue, fetal membranes, blood vessels and umbilical cords.
6. The method of claim 1 wherein the collagens comprise collagen types I, III, IV, V, VI and VII.
7. The method of claim 6 wherein the proteoglycans and glycosaminoglycans are solubilized and intact.
8. The method of claim 1 wherein the sterile extracellular connective tissue matrix composition comprises at least about 0.1% of said mixture.
9. The method of claim 1 wherein the sterile extracellular connective tissue matrix composition is applied at least about once a day to said damaged cornea.
10. The method of claim 1 wherein said composition comprising said sterile extracellular connective tissue matrix composition and said pharmaceutically acceptable carrier is applied to the cornea over a period of time sufficient to reduce the time required to complete the healing process of the damaged cornea.

11. A method of treating damaged cartilage tissue comprising applying to said damaged cartilage tissue a therapeutically effective amount of a composition comprising:
  (a) a sterile extracellular connective tissue matrix composition comprising collagens, proteoglycans, glycosaminoglycans and glycoproteins, wherein said collagens, said proteoglycans, said glycosaminoglycans, and said glycoproteins have each been extracted from an extracellular connective tissue matrix and are in their native structural form, and
  (b) a pharmaceutically acceptable carrier.

12. The method of claim 11 wherein the damage to the cartilage is caused by arthritis.

13. The method of claim 11 wherein the composition is provided to the damaged cartilage by intraarticular injection.

14. The method of claim 11 wherein the sterile extracellular connective tissue matrix composition is derived from a mammal.

15. The method of claim 11 wherein the sterile extracellular connective tissue matrix composition is derived from an animal selected from the group consisting of bovine, ovine and porcine.

16. The method of claim 14 wherein the sterile extracellular connective tissue matrix composition is derived from the tissue selected from the group consisting of placenta tissue, fetal membranes, blood vessels and umbilical cords.

17. The method of claim 11 wherein the collagens comprise collagen types I, III, IV, V, VI and VII.

18. The method of claim 11 wherein the proteoglycans and glycosaminoglycans are solubilized and intact.

19. The method of claim 11 wherein the sterile extracellular connective tissue matrix composition comprises at least about 0.1% of said mixture.

20. The method of claim 11 wherein the sterile extracellular connective tissue matrix composition is provided at least about once a day to said damaged cartilage.

21. The method of claim 11 wherein said composition comprising said sterile extracellular connective tissue matrix composition and said pharmaceutically acceptable carrier is provided to the cartilage over a period of time sufficient to reduce the time required to complete the healing process of the damaged cartilage.

22. A method for treating damaged uterine tissue comprising applying to said damaged uterine tissue a therapeutically effective amount of a composition comprising:
  (a) a sterile extracellular connective tissue matrix composition comprising collagens, proteoglycans, glycosaminoglycans and glycoproteins, wherein said collagens, said proteoglycans, said glycosaminoglycans, and said glycoproteins have each been extracted from an extracellular connective tissue matrix and are in their native structural form, and
  (b) a pharmaceutically acceptable carrier.

23. The method of claim 22 wherein the sterile extracellular connective tissue matrix composition and pharmaceutically acceptable carrier is applied topically.

24. The method of claim 22 wherein the sterile extracellular connective tissue matrix composition is derived from a mammal.

25. The method of claim 22 wherein the sterile extracellular connective tissue matrix composition is derived from an animal selected from the group consisting of bovine, ovine and porcine.

26. The method of claim 24 wherein the sterile extracellular connective tissue matrix composition is derived from the tissue selected from the group consisting of placenta tissue, fetal membranes, blood vessels and umbilical cords.

27. The method of claim 22 wherein the collagens comprise collagen types I, III, IV, V, VI and VII.

28. The method of claim 22 wherein the proteoglycans and glycosaminoglycans are solubilized and intact.

29. The method of claim 22 wherein the sterile extracellular connective tissue matrix composition comprises at least about 0.1% of said mixture.

30. The method of claim 22 wherein the sterile extracellular connective tissue matrix composition is applied at least about once a day to said damaged uterus.

31. The method of claim 22 wherein said composition comprising said sterile extracellular connective tissue matrix composition and said pharmaceutically acceptable carrier is applied to the uterine tissue over a period of time sufficient to reduce the time required to complete the healing process of the damaged uterine tissue.

* * * * *